United States Patent [19]

Reichenbacher

[11] 4,115,928
[45] * Sep. 26, 1978

[54] FREEZE-DRY PROCESS AND PRODUCT

[75] Inventor: Frank W. Reichenbacher, Scottsdale, Ariz.

[73] Assignee: Armour Pharmaceutical Company, Phoenix, Ariz.

[*] Notice: The portion of the term of this patent subsequent to Aug. 26, 1993, has been disclaimed.

[21] Appl. No.: 425,599

[22] Filed: Dec. 17, 1973

[51] Int. Cl.² .............................. F26B 5/06; F26B 5/04
[52] U.S. Cl. ................................................ 34/5; 34/92; 128/156; 128/334 R
[58] Field of Search ................... 34/5, 92; 128/334 R, 128/156 R

[56] References Cited

U.S. PATENT DOCUMENTS

| | | | |
|---|---|---|---|
| 3,233,333 | 2/1966 | Oppenheimer | 34/5 |
| 3,245,152 | 4/1966 | Natelson et al. | 34/5 |
| 3,789,515 | 2/1974 | Duprai | 34/5 |
| 3,842,831 | 10/1974 | Beisang et al. | 128/334 |

FOREIGN PATENT DOCUMENTS 1,459,130  10/1966  France ............................................ 34/5

Primary Examiner—John J. Camby
Attorney, Agent, or Firm—Charles E. Cates; Richard R. Mybeck

[57] ABSTRACT

An improvement in freeze-drying of skin tissue for use in treating wounds and diseased areas of the body wherein un-frozen skin is partially dried and frozen by drawing a vacuum across the skin before commencing the freeze-dry process, resulting in a novel product which reconstitutes more rapidly and more completely, and more nearly obtains the properties of fresh skin than obtainable by the product produced by the prior art process. In addition to the advantage of more efficient reconstitution, the method shortens the freeze-dry cycle and is less expensive.

18 Claims, No Drawings

FREEZE-DRY PROCESS AND PRODUCT

BACKGROUND OF THE INVENTION

1. Field of the Invention

This invention relates to freeze-dried animal skin tissue products, especially for therapeutic use on wounds, and to methods of producing such products. As used herein "skin" and "tissue" refer to whole or split thickness animal skin, porcine or human, unless otherwise indicated by context.

2. Description of the Prior Art

Generally, the lyophilization of skin tissue is accomplished by introducing frozen skin into a freeze-dry apparatus and performing a freeze-dry cycle, which may be summarized as drawing a vacuum, heating the tissue without thawing it to sublime the ice, removing the ice from proximity to the tissue, and gradually raising the temperature of the tissue to ambient temperature as it dries.

The prior art freeze-drying method as it pertains to skin for therapeutic use on humans uses skin tissue which first has been treated by other processes which remove dirt, debris, hair, and unwanted layers of the full thickness skin. Typically the skin is frozen, then irradiated with gamma rays, and stored temporarily in the frozen state to await freeze-drying. Later it is loaded by batches into a freeze-dry apparatus and the ice is sublimed and removed from the presence of the skin by warming the skin without thawing as it is gradually brought to room temperature. The dried product has about 0.5–5 weight % water. Descriptions of the details of representative prior art processes may be found in publications such as *British Journal of Hospital Medicine*, April 1971; "The Long-Term Storage of Skin," by T. D. Cochrane and John Watson; and "Description of Current Tissue Bank Methods of Skin Preservation," by Vernon P. Perry, *Cryobiology*, Vol. 3, No. 2, 1966.

The advantage of freeze-dried skin is that it can be stored for long periods of time at room temperatures until need arises. In this way therapeutic skin, for example, can be accumulated in quantities more conveniently in other forms such as frozen and fresh.

When needed the skin tissue can be rehydrated with water to a condition approaching that of fresh skin.

However, a problem in the prior art has been that the tissue produced by the prior art process approaches that of fresh skin on reconstitution, but not as closely as desired. The extent of reconstitution determines the ability of the skin to conform to the patient's affected part. The common therapeutic use of skin, as for example split thickness porcine skin, is as a bandage for extensive burn wounds. Here the suppleness, texture, and moistness of the skin, all of which are functions of the degree of reconstitution of it, are important to obtaining conformity to the body and mechanical adherence to the wound.

The more completely reconstituted the freeze-dried skin tissue, the more useful it is. Inasmuch as the prior art freeze-dried skin tissue falls short of the optimum product, a freeze-dried skin tissue which more fully reconstitutes is much desired.

Another problem in use centers around the time required for reconstitution of freeze-dried skin. In treating burns, time is a factor because the patient's essential bodily fluids are lost through the wound and the body is open to invasion by infectious organisms, at a time when the body defences are debilitated by shock. Prior art freeze-dried skin requires from one-half hour to an hour to reconstitute. Any reduction of this time requirement is an enormous benefit and much desired.

SUMMARY OF THE INVENTION

It has been discovered that the introduction of the alternative step of drawing a vacuum across unfrozen skin tissue instead of freezing it in the conventional manner yields an improved product which is more useful for application to wounds to be treated because it reconstitutes more quickly, it more closely resembles fresh skin texture and it conforms and adheres more readily to the contour of the treated area of the patient's body.

In the process of this invention the skin tissue is subjected to a vacuum, conveniently sufficient to freeze the skin. Thereafter, the skin is lyophilized as in the prior art process which, briefly, comprises warming the frozen skin to sublime the ice from the skin without thawing, removing water vapor from proximity to the skin and gradually bringing the skin temperature up to storage temperature ranges.

It may be sufficient to draw a vacuum on unfrozen skin without freezing, the freezing to be accomplished by means other than a low vacuum before commencing the freeze-dry cycle. For example, it may be sufficient to draw a vacuum not sufficient to freeze the tissue, but sufficient to condition the tissue by whatever principle the invention operates on. The skin may then be stored for later lyophilization. In this sense the method of this invention may be thought of as a pre-conditioning process, separate from lyophilization but in preparation for it.

The process also produces a savings in the time and expense required for the freeze-dried cycle which is a useful result of the invention.

DESCRIPTION OF THE PREFERRED EMBODIMENTS

The starting material of the process is skin tissue, human or animal, preferably a split thickness of porcine skin, which has been suitably trimmed, washed and treated to the extent desired. The skin is frozen and collected in a quantity convenient for processing. A batch to be processed is thawed to any convenient temperature, for example, at least above 0° C. and preferably between about 5° C. to about 30° C. The temperature is not critical and persons skilled in the art will know to thaw the skin without decomposing it.

The skin is subjected to a vacuum of less than 100 microns in a suitable freeze-dry apparatus which serves to refreeze the skin. The freezing temperature is not critical, but a convenient range is about −20° C. to about −40° C.

Then the ice of the frozen skin is sublimed in a manner known to the art by warming the skin, removing the sublimed ice by condensing on a colder area, and continuing until the temperature of the skin and the water content achieve stable values.

The figure 100 microns is not a critical limit. The vacuum to be drawn is a variable which depends upon the temperature change desired and as much may be calculated from existing tables and empirically verified. Thus, the parameters for freezing skin by drawing a vacuum can be determined without undue experimentation.

The process should work in any vacuum value ranging from less than about 4,500 microns down to about 10 microns. The upper limit is the point at which the vapor pressure of water exceeds the pressure of the chamber at freezing temperature. The lower range is the practical limit of the apparatus. A practical range of vacuum values is from about 3,000 microns to about 15 microns, and a preferred vacuum is less than 100 microns.

Neither is it necessary to first freeze the skin and thaw it, the critical step being the freezing of the skin by drawing a vacuum or, possibly, drawing the vacuum in an unfrozen state, with or without concurrent freezing, as will be postulated herein.

The following examples are cited to illustrate the invention and assist in the understanding of it.

EXAMPLE I

General Procedure

Three test rolls of frozen split-thickness porcine skin, prepared by steps outside the scope of this invention, were processed in the following manner in a Vacudyne freeze dryer, Model No. VPFD-DX. The test rolls were thawed in phase 1, then refrozen by subjecting them to a vacuum in phase 2, then gradually warmed by radiant heat under vacuum as the ice sublimed from the rolls in phase 3, and dried for two days to about 0.5 to 5 wt. % residual water. In the thawing phase, the temperatures of the shelf attained 40° C. at atmospheric pressure, at which time heating was discontinued. A vacuum was drawn from atmospheric to 1,000 microns in ten minutes during a vacuum freeze phase. The shelf temperature registered 32° C. at this point. The vacuum continued to be drawn to 140 microns, the shelf temperature being 2° C. Heating was recommenced to initiate a third phase of gradual warming and subliming of ice from the rolls, lasting about two days. During phase 3, the temperature of the shelf rose to 38° C. in about 14 hours and the vacuum was drawn to 50 microns. Shelf temperature gradually rose to 40° C., at which time the vacuum was below 50 microns and eventually the vacuum registered 16 microns. Shelf temperature was maintained at approximately 40° C. and the vacuum was maintained below the 40 micron level. During phase 3, the temperature of the condenser was maintained below −50° C.

1. Roll T8 was thawed to 26° C. in phase 1, was refrozen to −35° C. in phase 2, was warmed to 38° C. in phase 3 and stabilized to complete drying.

2. Roll T9 was thawed to 21° C. in phase 1, refrozen to −38° C. in phase 2, and warmed to 37° C. in phase 3 and maintained at approximately 37° C. to complete drying.

3. Roll T10 was thawed to 21° C. in phase 1, refrozen to −37° C. in phase 2, and warmed to 37° C. in the course of phase 3, and maintained at about 37° C. for drying completion.

EXAMPLE II

Sample lot 46-2 of porcine skin was divided into four groups and treated in the following fashion.

Groups NF and NFC, rolls of skin, were lyophilized in the freeze-dry cycle starting in the unfrozen state, the first step of which is to draw a vacuum which resulted in freezing the rolls, NFC had also been chloroformed. Groups F and FC were similarly processed in the frozen state.

None of the Groups was irradiated.

Reconstitution tests were conducted on the lyophilized skin. The results are tabluated in Table I. The graded scale of values is:

10 = Exactly like fresh skin
9 = Good, will conform well on patient
8 = Marginal, slightly stiff, will conform with effort
7 = Poor
5 = Only partly reconstituted
1 = Dry skin Table I

| Sample I.D. No. | | Length | Reconst. Time | Thickness | Grade |
|---|---|---|---|---|---|
| 46-2-FC-7 | (a) | 3'8" | 15 min. | 0.012" | 10 |
| | (b) | | | 0.012" | 10 |
| | (c) | | | 0.015" | 9.5 |
| | (d) | | | 0.025" | 7.0 |
| | (e) | | | 0.015" | 9.0 |
| 46-2-FC-17 | (a) | 4' | 15 min. | 0.010" | 9.5 |
| | (b) | | | 0.025" | 9.5 |
| | (c) | | | 0.012" | 9.5 |
| | (d) | | | 0.012" | 9.0 |
| | (e) | | | 0.015" | 9.0 |
| 46-2-NFC-7 | (a) | 4' | 15 min. | 0.012" | 10 |
| | (b) | | | 0.012" | 10 |
| | (c) | | | 0.010" | 10 |
| | (d) | | | 0.015" | 10 |
| | (e) | | | 0.015" | 9.7 |
| 46-2-NFC-17 | (a) | 4' | 15 min. | 0.025" | 10 |
| | (b) | | | 0.015" | 10 |
| | (c) | | | 0.015" | 9.5 |
| | (d) | | | 0.010" | 9.5 |
| | (e) | | | 0.030" | 9.0 |
| 46-2-F-2 | (a) | 4' | 15 min. | 0.012" | 8.5 |
| | (b) | | | 0.010" | 8.5 |
| | (c) | | | 0.010" | 8.5 |
| | (d) | | | 0.015" | 8.5 |
| | (e) | | | 0.020" | 8.5 |
| 46-2-F-7 | (a) | 4' | 15 min. | 0.010" | 9 |
| | (b) | | | 0.010" | 9 |
| | (c) | | | 0.010" | 9 |
| | (d) | | | 0.010" | 9 |
| | (e) | | | 0.010" | 9 |
| 46-2-NF-2 | (a) | 4' | 15 min. | 0.015" | 10 |
| | (b) | | | 0.012" | 10 |
| | (c) | | | 0.010" | 10 |
| | (d) | | | 0.010" | 10 |
| | (e) | | | 0.020" | 9.5 |
| 46-2-NF-7 | (a) | 4' | 15 min. | 0.025" | 10 |
| | (b) | | | 0.035" | 10 |
| | (c) | | | 0.030" | 10 |
| | (d) | | | 0.015" | 10 |
| | (e) | | | 0.010" | 9.8 |

In order of decreasing desireability, the groups rank in the following order:
1. Non-Frozen
2. Non-Frozen chloroform
3. Frozen chloroform
4. Frozen

EXAMPLE III

Similar tests using the protocol of Example II were conducted on rolls of skin which had been irradiated while frozen, then thawed and refrozen in the chamber by drawing a vacuum before commencing the lyophilization process. The results are shown in Table II.

Table II

| Test No. TB 46-3 I.D. No. | | Length | Reconst. Time | Thickness | Grade |
|---|---|---|---|---|---|
| 1 | (a) | 3'8" | 15 min. | 0.012" | 9.5 |
| | (b) | | | 0.012" | 9.5 |
| | (c) | | | 0.014" | 9.5 |
| | (d) | | | 0.012" | 9.5 |
| | (e) | | | 0.010" | 9.5 |
| 2 | (a) | 4'4" | 15 min. | 0.010" | 10 |
| | (b) | | | 0.010" | 10 |
| | (c) | | | 0.010" | 10 |
| | (d) | | | 0.010" | 10 |
| | (e) | | | 0.012" | 9.5 |
| 3 | (a) | 3'6" | 15 min. | 0.012" | 10 |
| | (b) | | | 0.010" | 10 |
| | (c) | | | 0.010" | 10 |

Table II-continued

| Test No. TB 46-3 I.D. No. | | Length | Reconst. Time | Thickness | Grade |
|---|---|---|---|---|---|
|   | (d) |   |   | 0.010" | 10 |
|   | (e) |   |   | 0.010" | 9.7 |
| 4 | (a) | 3'6" | 15 min. | 0.010" | 10 |
|   | (b) |   |   | 0.010" | 10 |
|   | (c) |   |   | 0.010" | 10 |
|   | (d) |   |   | 0.010" | 10 |
|   | (e) |   |   | 0.012" | 9.8 |

The reconstitution time of 15 minutes compares favorably with the prior art — required time of 30 minutes to one hour. In all cases the reconstituted skin of the above example was either identical or very close to the feel of fresh porcine skin.

The underlying physiological mechanism by which the process improves the product is not known. It might be theorized that drawing the vacuum on unfrozen skin opens pores and capillaries and interstitial spaces between the cells. As has been pointed out in the preferred embodiment the vacuum is employed to effect the freezing, but alternative methods of freezing might be successfully employed in lieu of or in augmentation of the vacuum freezing. The subjecting of the skin or other animal tissue to a vacuum may be the crux of the invention in which case it might not be necessary to freeze the tissue while the skin is still subject to vacuum. It might be that the mechanism of the invention is the drawing of water-soluble materials to the surface of the skin during the vacuum drying preceding the sublimation operations, and that the deposit of the water-soluble materials aids reconstitution. In that event, vacuum drying without freezing might yield the product of this invention.

In any event the end product of this invention is skin having greater flexibility than the prior art process skin; this means that the skin conforms to the patient's body more readily and results in a better take upon application in a therapeutic use.

An example is as follows.

EXAMPLE IV

Fresh porcine split thickness skin having a temperature of 26° C. is subjected to a vacuum of 1,000 microns in a freeze-dry apparatus. This results in a frozen skin having an internal temperature of −8° C. The skin thus preconditioned is lyophilized by subjecting it to a standard freeze-dry cycle. The resulting skin product closely resembles unfrozen, natural porcine skin in the properties of degree of hydration, suppleness, appearance and feel upon reconstitution.

The examples above are illustrative of the method and product of this invention. Variations and equivalents within the scope of the invention will be apparent to those skilled in the art, and the invention is to be limited only by the appended claims.

What is claimed is:

1. A method of drying unfrozen animal skin tissue comprising the steps of freezing said tissue by drawing a vacuum across the tissue and thereafter lyophilizing said tissue.

2. The method of claim 1 in which said animal skin tissue has not previously been frozen.

3. The method of claim 2 wherein said skin is human.

4. The method of claim 2 wherein the skin is porcine.

5. A method according to claim 1 in which said unfrozen animal tissue is thawed tissue which had previously been frozen.

6. The process of claim 5 practiced on human skin.

7. The process of claim 5 wherein said skin is porcine.

8. A process of conditioning animal skin tissue for lyophilization comprising the step of subjecting said tissue to a vacuum.

9. The process of claim 1 wherein said vacuum is not more than about 4,500 microns.

10. The process of claim 1 wherein said vacuum is less than 100 microns.

11. The process of claim 1 wherein the temperature of said tissue is reduced by vacuum to below freezing.

12. The process of claim 1 wherein the temperature of said tissue is reduced by vacuum to between −20° C. and −40° C.

13. In a method of freeze drying skin tissue comprising the steps of drawing a vacuum across frozen tissue and thereafter subliming the ice from the frozen tissue, the improvement comprising drawing the vacuum across unfrozen tissue instead of frozen tissue.

14. The method of claim 13 wherein the temperature of unfrozen tissue is between about 5° C. and about 30° C.

15. The method of claim 1 wherein the temperature of the unfrozen tissue is between about 5° C. and about 30° C.

16. In a method of drying animal skin tissue, the improvement comprising the step of partially drying the tissue by drawing a vacuum across the tissue in an unfrozen state.

17. The method of claim 13 wherein the temperature of the unfrozen tissue is reduced from ambient temperature to above freezing by the vacuum.

18. The method of claim 13 wherein the unfrozen tissue is not frozen by the operation of the vacuum.

* * * * *